US 6,723,217 B1

(12) United States Patent
Duce et al.

(10) Patent No.: US 6,723,217 B1
(45) Date of Patent: Apr. 20, 2004

(54) METHOD AND DEVICE FOR PUMPING OXYGEN INTO A GAS SENSOR

(75) Inventors: Richard W. Duce, Flushing, MI (US); Paul C. Kikuchi, Fenton, MI (US); Wayne M. Chadwick, Grand Blanc, MI (US); Eric J. Detwiler, Davison, MI (US); Jeffrey T. Coha, Greenwood, IN (US); Carlos A. Valdes, Flint, MI (US); Scott T. Sanford, Clarkston, MI (US); Richard C. Kuisell, Lapeer, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/089,322
(22) PCT Filed: Oct. 20, 2000
(86) PCT No.: PCT/US00/41358
§ 371 (c)(1), (2), (4) Date: Jul. 23, 2002
(87) PCT Pub. No.: WO01/29546
PCT Pub. Date: Apr. 26, 2001

Related U.S. Application Data
(60) Provisional application No. 60/160,734, filed on Oct. 20, 1999.

(51) Int. Cl.[7] ..................... G01N 27/409; G01N 27/141
(52) U.S. Cl. .................. 204/429; 204/424; 204/425; 156/60; 156/89.12
(58) Field of Search ................. 204/421–429; 156/60, 89.12

(56) References Cited
U.S. PATENT DOCUMENTS
4,559,126 A * 12/1985 Mase et al.
4,647,364 A * 3/1987 Mase et al.
5,028,309 A * 7/1991 Nishizawa et al.
5,236,569 A * 8/1993 Murase et al.
5,800,689 A * 9/1998 Hori et al.
6,036,841 A * 3/2000 Kato et al.
6,156,176 A * 12/2000 Sugiyama et al.
6,227,033 B1 5/2001 Kainz
6,382,198 B1 5/2002 Smith et al.
6,453,726 B1 9/2002 Gutierrez et al.
6,484,561 B2 11/2002 Jackson et al.
6,514,397 B2 2/2003 LaBarge et al.
6,544,467 B2 4/2003 Symons et al.
6,562,747 B2 5/2003 Symons et al.
6,579,435 B2 6/2003 Wang et al.
6,579,436 B2 6/2003 Wang et al.
6,585,872 B2 7/2003 Donelon et al.

FOREIGN PATENT DOCUMENTS
EP 0841562 * 5/1998
EP 0845669 * 6/1998

* cited by examiner

Primary Examiner—Kaj K. Olsen
(74) Attorney, Agent, or Firm—Jimmy L. Funke (57) ABSTRACT

A gas sensor is created comprising an electrochemical cell having a solid electrolyte layer disposed between an exhaust gas electrode and a reference electrode. A resistor is disposed in electrical communication with a heater and the reference electrode. The resistor can be disposed on a side of the gas sensor; on a side of the gas sensor such that the resistor is electrically connected through a via hole; over at least a portion of at least two sides of the gas sensor; or disposed in a void extending at least from the heater to the pump electrode, such that the void extends to at least a surface of the gas sensor, extends to at least partially through the gas sensor, or extends completely through the gas sensor. A method for using this gas sensor comprises applying a voltage to the heater within the gas sensor. A current is directed through the resistor to the reference electrode to pump oxygen into the reference electrode.

35 Claims, 4 Drawing Sheets

METHOD AND DEVICE FOR PUMPING OXYGEN INTO A GAS SENSOR

CROSS REFERENCE TO RELATED APPLICATIONS

This case claims the benefit of the filing date of the provisional application U.S. Provisional Application Ser. No. 60/160,734, filed Oct. 20, 1999 that is hereby incorporated by reference in its entirety.

TECHNICAL FIELD

The present invention relates to exhaust gas sensors. More particularly, the present invention relates to an oxygen sensor.

BACKGROUND OF THE INVENTION

The automotive industry has used exhaust gas sensors in automotive vehicles for many years to sense the composition of exhaust gases, namely, oxygen. For example, a sensor is used to determine the exhaust gas content for alteration and optimization of the air to fuel ratio for combustion.

One type of sensor uses an ionically conductive solid electrolyte between porous electrodes. For oxygen, solid electrolyte sensors are used to measure oxygen activity differences between an unknown gas sample and a known gas sample. In the use of a sensor for automotive exhaust, the unknown gas is exhaust and the known gas, (i.e., reference gas), is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("exhaust gas electrode"), and a porous electrode exposed to a known gas' partial pressure ("reference electrode"). Sensors typically used in automotive applications use a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

For example, an oxygen sensor, with a solid oxide electrolyte such as zirconia, measures the oxygen activity difference between an unknown gas and a known reference gas. Usually, the known reference gas is the atmosphere air while the unknown gas contains the oxygen with its equilibrium level to be determined. Typically, the sensor has a built in reference gas channel which connects the reference electrode to the ambient air. To avoid contamination of the reference air by the unknown gas, the sensor requires expensive sensor package that usually has complex features in order to provide sufficient gas sealing between the reference air and the unknown gas. Historically, these gas sealed sensor packages have demonstrated insufficient durability in the field. This problem can be avoided by using in-situ electrochemical oxygen pumping. In this method, the air reference electrode chamber is replaced by a sealed reference electrode with oxygen electrochemically pumped in from the exhaust gas. This method eliminates the exhaust gas contamination problem but creates its own drawbacks. That is, an expensive electronic circuit is required to do the electrochemical oxygen pumping.

What is needed in the art is a simplified gas sensor that employs an electrochemical pumping of oxygen.

SUMMARY OF THE INVENTION

The deficiencies of the above-discussed prior art are overcome or alleviated by the gas sensor and method of producing the same.

One embodiment of the sensor comprises an electrochemical cell having a solid electrolyte layer disposed between an exhaust gas electrode and a reference electrode. At least one protective layer is disposed in contact with the exhaust gas electrode with at least one via hole is disposed through the protective layer, and at least one reference gas channel is disposed in fluid communication with the reference electrode. Disposed in thermal communication with the electrochemical cell is a heater, with a resistor disposed in electrical communication with the heater and a pump electrode.

One embodiment of the method of using a gas sensor comprises disposing an electrochemical cell having a solid electrolyte between an exhaust gas electrode and a reference electrode. Disposing at least one protective layer in contact with the exhaust gas electrode at least one via hole through the protective layer, and at least one reference gas channel in fluid communication with the reference electrode. A heater is positioned in thermal communication with the electrochemical cell, and a resistor is disposed in electrical communication with the heater and a pump electrode and applying a voltage to the sensor.

The above discussed and other features and advantages of the present invention will be appreciated and understood by those skilled in the art from the following detailed description and drawings.

BRIEF DESCRIPTION OF THE DRAWINGS

The present invention will now be described, by way of example only, with reference to the accompanying drawings, which are meant to be exemplary, not limiting, and wherein like elements are numbered alike in several figures, in which.

DETAILED DESCRIPTION OF INVENTION

Normal sensor operations and a clean air reference are maintained by pumping oxygen into the reference electrode during operation. The sensor element needs a power supply to pump oxygen from the reference electrode to the exhaust gas electrode. The current used to pump the oxygen can be derived from the heater supply. The current travels first through a current limiting resistor that reduces the current to an acceptable level prior to reaching the reference electrode. Upon application of the current, oxygen is pumped through the solid electrolyte layer from the exhaust gas electrode to the reference electrode since the electrolyte is ionically conductive to oxide ions.

Figure 1:
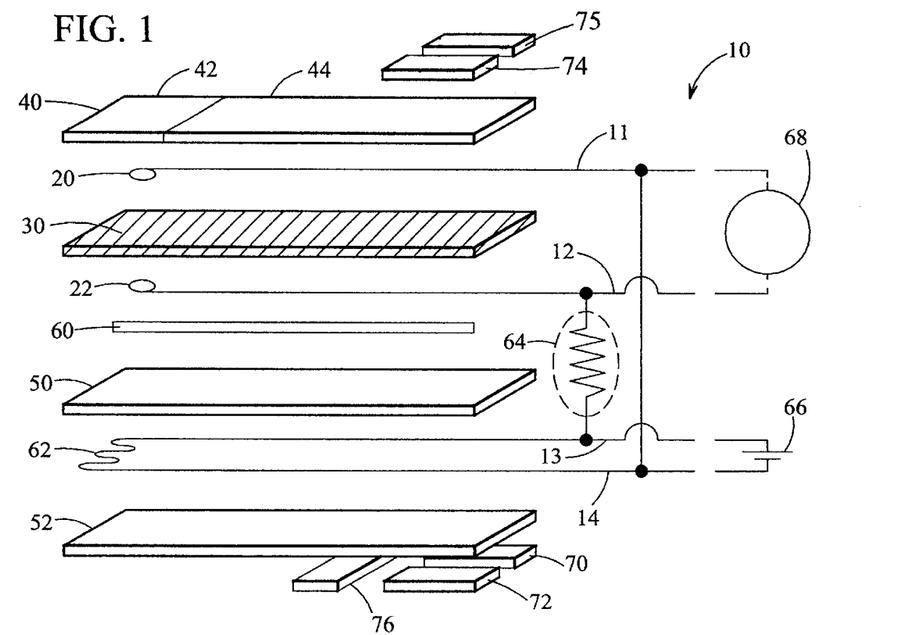
FIG. 1 is an expanded side view of a gas sensor design and an associated electrical schematic.

Referring to FIG. 1, the sensor element 10 is illustrated. The exhaust gas (or outer) electrode 20 and the reference gas (or inner) electrode 22 are disposed on opposite sides of, and adjacent to, a solid electrolyte layer 30 creating an electrochemical cell (20/30/22). On the side of the exhaust gas electrode 20 opposite solid electrolyte 30 is a protective insulating layer 40 having a dense section 44 and a porous section 42 that enables fluid communication between the exhaust gas electrode 20 and the exhaust gas. Meanwhile, disposed on the side of the reference electrode 22 opposites solid electrolyte 30 is a reference gas channel 60 which is in fluid communication with the reference electrode 22 and optionally with the ambient atmosphere and/or the exhaust gas. Disposed on a side of the reference gas channel 60 opposite the reference electrode 22 is a heater 62 for maintaining sensor element 10 at the desired operating temperature. Typically disposed between the reference gas channel 60 and the heater 62, as well as on a side of the heater opposite the reference gas channel 60, are one or more insulating layers 50, 52. Finally, disposed on the exterior surfaces of the sensor are contact pads 70, 72, 74, 75, 76.

Furthermore, to provide electrical communication, several leads are employed. Lead 11 is in electrical communication with an exhaust gas electrode 20. Lead 12 electrically communicates with the reference electrode 22, heater 62 and a power supply 66. Both leads 11 and 12 are also in electrical communication with the volt meter 68, while leads 13 and 14 are in electrical communication with the heater 62 and the power supply 66. Disposed between and electrically connecting leads 12 and 13 is a current limiting resistor 64.

Figure 2:
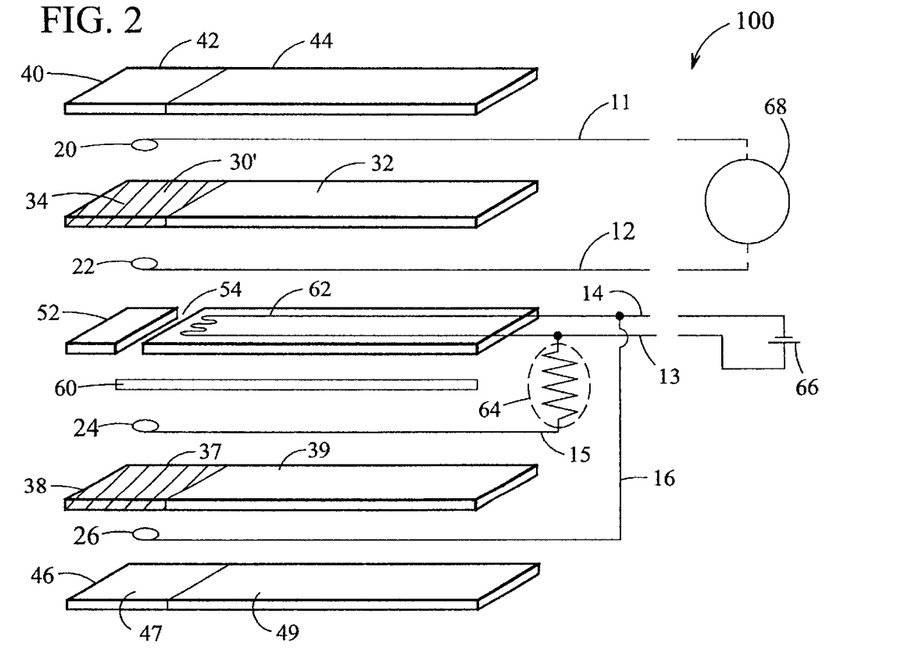
FIG. 2 is an expanded side view of a gas sensor design and an associated electrical schematic.

Referring to FIG. 2, the sensor element 100 is illustrated. Sensor element 100 is illustrated with similar parts as sensor element 10, with the following deviations. Electrolyte layer 34 is comprised of an electrolyte portion 30'0 and an insulating portion 32. Pump electrodes 24, 26 are disposed on opposite sides of an electrolyte layer 38, having an electrolyte portion 37 and an insulating portion 39 creating an oxygen pump cell. Pump electrode 24 is preferably disposed adjacent to reference gas channel 60 or at least in fluid communication therewith. Insulating layer 52 has a channel (slit, hole, aperture, or the like) 54 to provide for fluid communication between the reference gas channel 24 and the reference electrode 22. A heater 62 is provided on insulating layer 52 in thermal communication with reference electrode 22. Meanwhile, another protective insulating layer 46, having a porous section 47 and a dense section 49, is provided adjacent to pump electrode 26.

As with the above embodiment, electrical communication is established amongst various electrodes and the heater via several leads. Lead 11 is in electrical communication with the exhaust gas electrode 20, lead 12 is in electrical communication with the reference electrode 22, leads 13 and 14 are in electrical communication with the heater 62, lead 15 is electrically connected with pump electrode 24 and lead 16 is in electrical communication with pump electrode 26. A current limiting resistor 64 is located between lead 15 and the heater positive lead 13. In addition to connecting to the respective electrodes and heater, leads 11 and 12 are in electrical communication with voltmeter 68, leads 13 and 14 (i.e. positive and negative leads, respectfully) are connected to power supply 66, and lead 14 is in electrical communication with lead 16.

Figure 3:
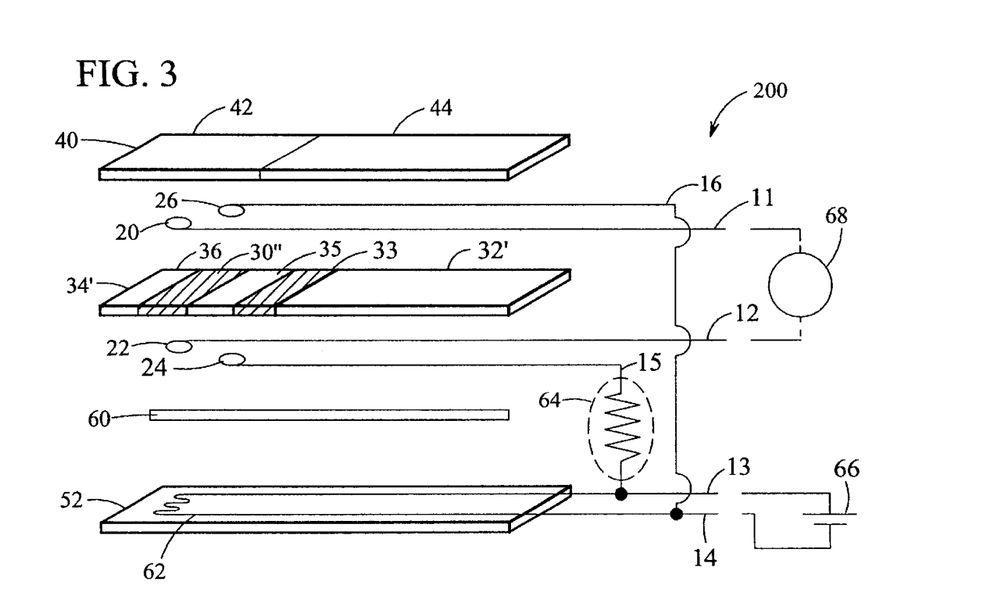
FIG. 3 is an expanded side view of a gas sensor design and an associated electrical schematic.

In FIG. 3, yet an alternative embodiment is illustrated. Sensor element 200 is illustrated with similar parts as sensor elements 10 and 100, with the following deviations. Pump electrode 26 is disposed adjacent to the exhaust gas electrode 20 and the electrolyte layer 34'. The electrolyte layer 34' is comprised of two electrolyte portions 30" and 33 disposed between three insulating portions 32', 35, 36. Both the reference electrode 22 and the pump electrode 24 are disposed between the electrolyte layer 34' and the insulating layer 52 in fluid communication with the reference gas channel 60. A heater 62 is provided on the insulating layer 52 in thermal communication with the electrochemical cell 20/34'/22. As above, leads 11 and 12 are in electrical communication with electrodes 20 and 22, respectively, and with volt meter 68 while leads 15, 16 are in electrical communication with electrodes 24, 26, respectively. Leads 13 and 14 are in electrical communication with heater 62 and power source 66. Leads 13, 14 are further in electrical communication with leads 15, 16, respectively, with electrical communication between lead 15 and positive lead 13 being via resistor 64.

The gas sensor components, i.e., protective layers 40, 46, electrodes 20, 22, 24, 26 (and leads thereto), heater 62, and insulating layers 50, 52 are conventional components in a gas sensor. Furthermore, in addition to these conventional components, additional conventional components can be employed, including but not limited to additional protective coatings (e.g., spinel, alumina, magnesium aluminate, and the like, as well as combinations comprising at least one of the foregoing coatings), lead gettering layer(s), ground plane (s), support layer(s), additional electrochemical cell(s), and the like. The leads, which supply current to the heater and electrodes, are typically formed on the same layer as the heater/electrode to which they are in electrical communication and extend from the heater/electrode to the terminal end of the gas sensor where they are in electrical communication with the corresponding via (not shown) and appropriate contact pad(s) 70, 72, 74, 75, 76, 79.

Insulating layers 50, 52, and any support layers, are typically capable of: providing structural integrity (e.g., effectively protecting various portions of the gas sensor from abrasion, vibration, and the like, and providing physical strength to the sensor); and physically separating and electrically isolating various components. The insulating layer (s), which can be formed using ceramic tape casting methods or other methods such as plasma spray deposition techniques, screen printing, stenciling and others conventionally used in the art, can each be up to about 200 microns thick, with a thickness of about 50 microns to about 200 microns preferred. Typically these insulating layers comprise a dielectric material such as alumina and the like. Since the materials employed in the manufacture of gas sensor preferably comprise substantially similar coefficients of thermal expansion, shrinkage characteristics, and chemical compatibility in order to minimize, if not eliminate, delamination and other processing problems, the particular material, alloy or mixture chosen for the insulating layer is dependent upon the specific electrolyte employed.

On a side of the reference gas channel 60 opposite the reference electrode, typically disposed between two insulating layers, e.g., 50, 52, is a heater 62 which is employed to maintain the sensor element at the desired operating temperature. Heater 62 can be any conventional heater capable of maintaining the sensor end at a sufficient temperature to facilitate the various electrochemical reactions therein. The heater 62, which is typically platinum, alumina, palladium, and the like, as well as mixtures and alloys comprising at least one of the foregoing metals, or any other conventional heater, is generally screen printed onto a substrate to a thickness of about 5 microns to about 50 microns.

The heater maintains the electrochemical cell (electrodes 20, 22 and electrolyte 30) at a desired operating temperature. The electrolyte layers 30, 30', 30", 33, and 37, are preferably a solid electrolyte that can comprise the entire layer or a portion thereof (see FIGS. 1–3), can be any material that is capable of permitting the electrochemical transfer of oxygen ions while inhibiting the physical passage of exhaust gases, has an ionic/total conductivity ratio of approximately unity, and is compatible with the environment in which the gas sensor will be utilized (e.g., up to about 1,000° C.). Possible solid electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as combinations comprising at least one of the foregoing. For example, the electrolyte can be alumina and yttrium stabilized zirconia. Typically, the solid electrolyte, which can be formed via many conventional processes (e.g., die pressing, roll compaction, stenciling and screen printing, tape casting techniques, and the like), has a thickness of up to about 500 microns, with a thickness of approximately 25 microns to about 500 microns preferred, and a thickness of about 50 microns to about 200 microns especially preferred.

It should be noted that, in some embodiments, a porous electrolyte may also be employed. The porous electrolyte should be capable of permitting the physical migration of exhaust gas and the electrochemical movement of oxygen ions, and should be compatible with the environment in which the gas sensor is utilized. Typically, porous electrolyte has a porosity of up to about 20%, with a median pore size of up to about 0.5 microns, or, alternatively, comprises a solid electrolyte having one or more holes, slits, or apertures therein, so as to enable the physical passage of exhaust gases. Commonly assigned U.S. Pat. No. 5,762,737 to Bloink et al., which is hereby incorporated in its entirety by reference, further describes porous electrolytes that may be useful in the instant application. Possible porous electrolytes include those listed above for the solid electrolyte.

It should be noted that the electrolyte layers 30, 30', 30", 33, and 37, as well as protective layers 40 and 46, can comprise entire layer or any portion thereof, e.g., they can form the layer, be attached to the layer (protective material/electrolyte abutting dielectric material), or disposed an opening in the layer (protective material/electrolyte can be an insert in an opening in a dielectric material layer). The latter arrangement eliminates the use of excess electrolyte and protective material, and reduces the size of gas sensor by eliminating layers. Any shape can be used for the electrolyte and protective material, with the size and geometry of the various inserts, and therefore the corresponding openings, being dependent upon the desired size and geometry of the adjacent electrodes. It is preferred that the openings, inserts, and electrodes have a substantially similar geometry.

The various electrodes 20, 22, 24, and 26 are disposed on opposites sides of an in ionic contact with electrolyte layers 30, 30', 30", 33, and 37 (see FIGS. 1–3), as well as any porous electrolyte. These electrodes can comprise any catalyst capable of ionizing oxygen, including, but not limited to, metals such as platinum, palladium, osmium, rhodium, iridium, gold, and ruthenium; metal oxides such as zirconia, yttria, ceria, calcia, alumina and the like; other materials, such as silicon, and the like; and mixtures and alloys comprising at least one of the foregoing catalysts. As with the electrolyte, the electrodes 20, 22 can be formed using conventional techniques. Some possible techniques include sputtering, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. For example, reference electrode 22 can be screen printed onto insulating layer 50 or over the solid electrolyte 30, while exhaust electrode 20 can be screen printed over solid electrolyte 30 or on protective layer 40. Electrode leads 14 and vias (not shown) in the insulating and/or electrolyte layers (not shown) are typically formed simultaneously with electrodes.

Disposed in fluid communication with the reference electrode 22 is the reference gas channel 60 formed by depositing a fugitive material, e.g. carbon base material such as carbon black, such that upon processing the material burns out, and leaves a void. This fugitive material can be employed alone or in conjunction with an oxygen storage material. Possible oxygen storage materials include precious metals, alkaline materials, and the like, as well as combinations and alloys comprising at least one of the foregoing oxygen storage materials.

The sensor comprising the above-described components can be formed in any conventional fashion, with co-firing the various components preferred. In this embodiment, a post-sintering application of resistive ink should be used to integrate the resistor into or on the sensor element. The processes that can be used to deposit the resistive ink into/on the sensor element include screen printing, pad printing, stencil printing, sputtering, bladder filling, and the like. Post ink application, the sensor element is typically fired at a sufficient temperature to remove solvents, organics, binders, and plasticizers, and to melt the lead-based glass preferably employed in the ink. Typically, temperatures of up to about 850° C. or so for up to about one hour with up to about 10 minutes, are sufficient. The specific firing temperature and duration are dependent upon the resistive ink used. The resistive ink typically comprises a solution or slurry of a metal oxide having the desired resistivity. Possible metal oxides include ruthenium oxide, tin oxide, zinc oxide, and indium oxide as well as mixtures and alloys comprising at least one of the foregoing metal oxides. Metal-based nitride inks or boride inks, such as lanthanum boride, may also be used. However, a resistive ink material that meets the resistance requirements may also be used.

With the arrangements provided in FIGS. 1–3, a voltage divide occurs between the resistor and the electrochemical cell. A small amount of voltage is applied to the reference electrode that results in the electrochemical pumping of oxygen through the electrolyte layer into the reference electrode. To ensure that oxygen flows towards the reference electrode, the reference electrode should be positively polarized. The electrolyte layer is ionically conductive to the oxide ions and therefore pumps the oxygen from the exhaust gas electrode to the reference electrode to maintain a clean air reference. A small bias voltage will result across the electrochemical cell from the current being produced from the ionic oxygen flow into the reference electrode. The amount of current generated is about 1 microamperes ($\mu A$) to about 100 $\mu A$. A common ground, within the sensor element or external to the sensor should be provided between the sensor circuitry and the heater circuitry.

Figure 4:
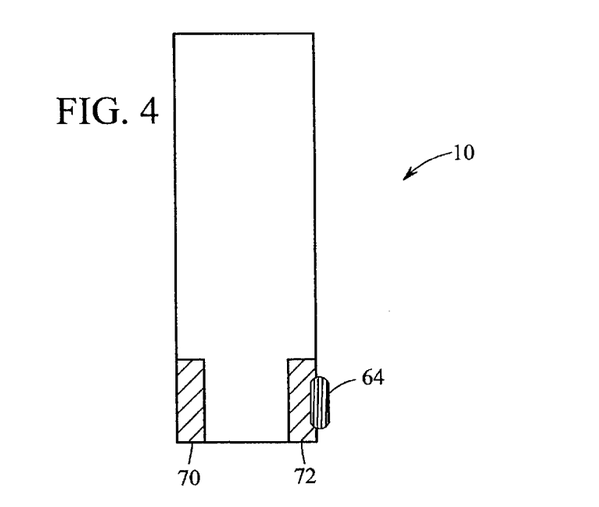
FIG. 4 is a top view of a sensor element with a resistor.
Figure 5:
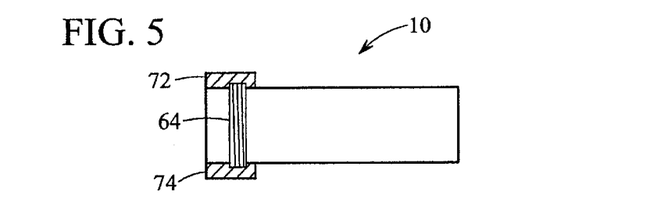
FIG. 5 is an exploded side view of the sensor element in FIG. 4.

The resistor should be positioned such that electrical communication is achieved between the positive heater lead and the reference electrode. FIGS. 4 and 5 illustrate the disposing or placing of the current limiting resistor along the edge or side of the sensor element. FIG. 4 illustrates the top view with the current limiting resistor 64 printed along the exterior side of the sensor element 10 near contact pad 72. The contact pad 70, on the face of the sensor element 10 is also illustrated. FIG. 5 illustrates the side view with the current limiting resistor 64 printed along the exterior side of the sensor element 10 near contact pads 72, 74.

Figure 6:
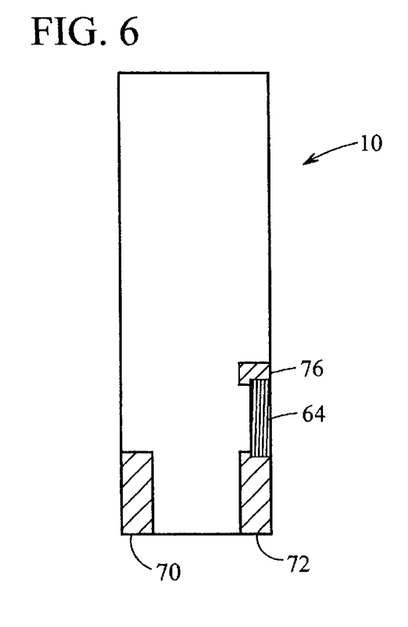
FIG. 6 is another top view of a sensor element with a resistor.

FIG. 6 illustrates disposing or placing the current limiting resistor 64 along an exterior face (or side) of the sensor element 10, printed adjacent to contact pads 72, 76. In this embodiment, electrical connection to the heater is achieved by "tunneling" through the sensor element 10 by a via hole located under contact pad 76.

Figure 7:
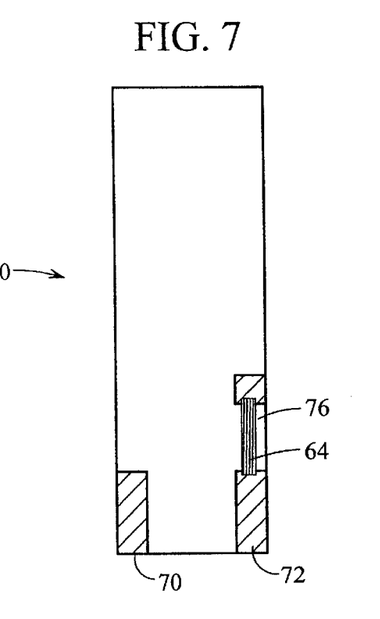
FIG. 7 is a third top view of a sensor element with a resistor.
Figure 8:
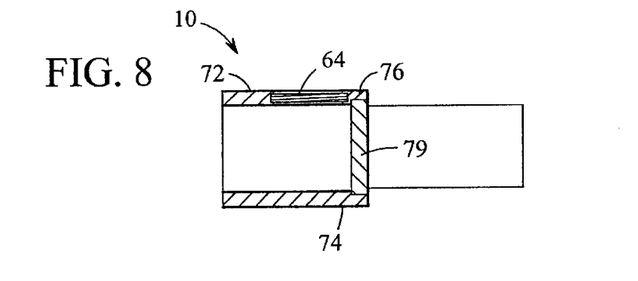
FIG. 8 is an exploded side view of the sensor element in FIG. 7.

FIGS. 7 and 8 illustrate disposing or placing the current limiting resistor 64 along an exterior face (or side) of the sensor element 10. FIG. 7 illustrates the current limiting resistor 64 printed adjacent to contact pads 72, 76. The contact pad 70, on the face of the sensor element 10 is also illustrated. FIG. 8 illustrates the current limiting resistor 64 printed adjacent to the contact pads 72, 76. In this embodiment, electrical connection to the heater is achieved by disposing around or wrapping around the contact pad 79 from contact pad 76 to contact pad 74, such that the resistor 64 is in contact with two sides of the sensor element 10.

Figure 9:
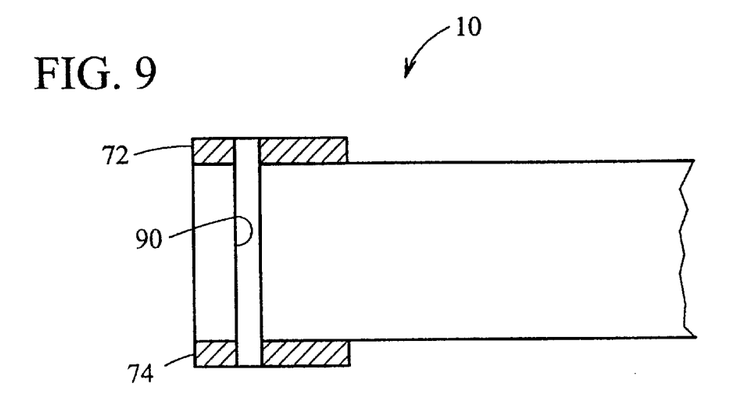
FIG. 9 is an exploded side view of a sensor element with a void.

FIG. 9 illustrates creating, burrowing or punching an opening, hole, cavity or void 90 into the interior of the sensor element 10 for eventual placement of the current limiting resistor. The void 90 that is created may extend completely or partially through the sensor element. The void 90 is created through the sensor element 10 prior to sintering. The contact pads 72, 74 are also illustrated. The void 90 is positioned such that no critical functions (i.e. air reference chamber integrity, electrode performance) are unacceptably impacted.

Figure 10:
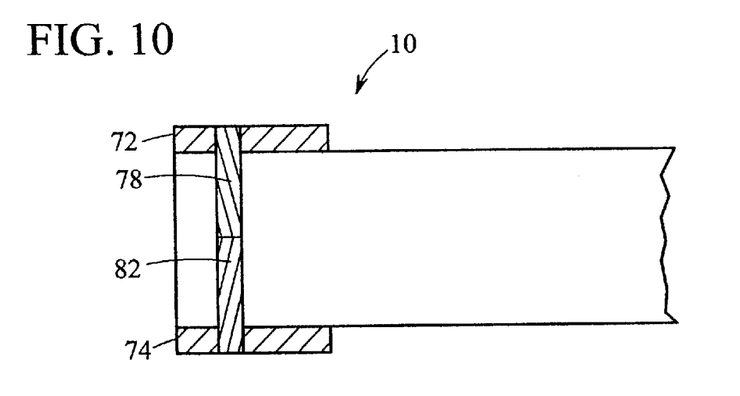
FIG. 10 is a representation of FIG. 9 with the void filled with resistive ink.

FIG. 10 illustrates disposing a resistive ink 82 in the interior of the sensor element 10 created in FIG. 9. The resistive ink 82 can completely or partially fill the punched void 90. A conductive material 78, such as platinum, can be used to fill the remaining space not occupied by the resistive ink to provide for electrical communication with the contact pads. The sensor element is then fired again creating the current limiting resistor.

With the design of the gas sensor, electricity is used to pump oxygen electrochemically from the exhaust gas electrode to the reference electrode. By pumping oxygen into the reference electrode, a clean air reference is maintained. A heater supplies the necessary power, through a current limiting resistor, eliminating the need for an additional power supply and electronic circuit.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

What is claimed is:

1. A gas sensor comprising:
   an electrochemical cell having a solid electrolyte layer disposed between an exhaust gas electrode and a reference electrode;
   a protective layer disposed in contact with the exhaust gas electrode;
   a via hole disposed through the protective layer;
   a reference gas channel disposed in fluid communication with the reference electrode;
   a heater disposed in thermal communication with the electrochemical cell, wherein the heater is in electrical communication with a positive lead and a negative lead; and
   a resistor disposed in electrical communication between the positive lead and a first pump electrode.

2. The gas sensor of claim 1, wherein the resistor is disposed on a side of the gas sensor.

3. The gas sensor of claim 1, wherein the resistor is disposed on a side of the gas sensor wherein the resistor is electrically connected to the heater through the via hole.

4. The gas sensor of claim 1, wherein at least a portion of the resistor is disposed over at least two sides of the gas sensor.

5. The gas sensor of claim 1, further comprising a void extending at least from the heater to the first pump electrode.

6. The gas sensor of claim 5, wherein the void extends to at least a surface of the gas sensor.

7. The gas sensor of claim 5, wherein the void extends from a first surface of the gas sensor to a second surface of the gas sensor.

8. The gas sensor of claim 1, wherein the solid electrolyte layer is comprised of zirconia.

9. The exhaust gas sensor of claim 1, further comprising a second pump electrode, wherein the first pump electrode and the second pump electrode are disposed on opposite sides of the solid electrolytes.

10. The exhaust gas sensor of claim 1, further comprising a second pump electrode and a second electrolyte, wherein the first pump electrode and the second pump electrode are disposed on opposite sides of the second electrolyte to form a pump cell, and wherein the pump cell is disposed on a side of the reference gas chamber opposite the reference electrode.

11. A method of making a gas sensor comprising:
disposing an electrochemical cell having a solid electrolyte layer between an exhaust gas electrode and a reference electrode;
disposing a protective layer in contact with the exhaust gas electrode;
disposing a via hole through the protective layer;
disposing a reference gas channel in fluid communication with the reference electrode;
disposing a heater in thermal communication with the electrochemical cell, wherein the heater is in electrical communication with a positive lead and a negative lead; and
disposing a resistor in electrical communication between the positive lead and a pump electrode.

12. The method making of a gas sensor of claim 11, further comprising disposing the resistor on a side of the gas sensor.

13. The method of making of a gas sensor of claim 11, further comprising disposing the resistor on a side of the gas sensor wherein the resistor is electrically connected to the heater through the via hole.

14. The method of making of a gas sensor of claim 11, further comprising disposing at least a portion of the resistor over at least two sides of the gas sensor.

15. The method of making of a gas sensor of claim 11, further comprising disposing a void extending at least from the heater to the pump electrode.

16. The method of making of a gas sensor of claim 15, further comprising disposing the void to at least a surface of the gas sensor.

17. The method of making of a gas sensor of claim 16, further comprising disposing the void from a first surface of the sensor to a second surface of the sensor.

18. A gas sensor comprising:
an electrochemical cell having a solid electrolyte layer disposed between an exhaust gas electrode and a reference electrode;
a protective layer disposed in contact with the exhaust gas electrode;
a via hole disposed through the protective layer;
a reference gas channel disposed in fluid communication with the reference electrode;
a heater disposed in thermal communication with the electrochemical cell, wherein the heater is in electrical communication with a positive lead and a negative lead; and
a resistor disposed in electrical communication between the positive lead and the reference electrode.

19. The gas sensor of claim 18, the resistor is disposed on a side of the gas sensor.

20. The gas sensor of claim 18, wherein the resistor is disposed on a side of the gas sensor wherein the resistor is electrically connected through the via hole.

21. The gas sensor of claim 18, wherein at least a portion of the resistor is disposed over at least two sides of the gas sensor.

22. The gas sensor of claim 18, further comprising a void extending at least from the heater to the reference electrode.

23. The gas sensor of claim 22, wherein the void extends to at least a surface of the gas sensor.

24. The gas sensor of claim 22, wherein the void extends from a first surface of the gas sensor to a second surface of the gas sensor.

25. A method of making a gas sensor comprising:
disposing an electrochemical cell having a solid electrolyte layer between an exhaust gas electrode and a reference electrode;
disposing a protective layer in contact with the exhaust gas electrode;
disposing a via hole through the protective layer;
disposing a reference gas channel in fluid communication with the reference electrode;
disposing a heater in thermal communication with the electrochemical cell, wherein the heater is in electrical communication with a positive lead and a negative lead; and
disposing a resistor in electrical communication between the positive lead and the reference electrode.

26. The method of making a gas sensor of claim 25, further comprising disposing the resistor on a side of the gas sensor.

27. The method of a gas sensor of claim 25, further comprising disposing the resistor on a side of the gas sensor wherein the resistor is electrically connected to the heater through the via hole.

28. The method of making a gas sensor of claim 25, further comprising disposing at least a portion of the resistor over at least two sides of the gas sensor.

29. The method of making a gas sensor of claim 25, further comprising disposing a void extending at least from the heater to the pump electrode.

30. The method of making a gas sensor of claim 29, further comprising disposing the void to at least a surface of the gas sensor.

31. The method of making a gas sensor of claim 30, further comprising disposing the void from a first surface of the sensor to a second surface of the sensor.

32. A gas sensor comprising:
an electrochemical cell having a solid electrolyte layer disposed between an exhaust gas electrode and a reference electrode;
a protective layer disposed ill contact with the exhaust gas electrode;
a via hold disposed through the protective layer;
a reference gas channel disposed in fluid communication with the reference electrode;
a heater disposed in thermal communication with tho electrochemical cell; and
a resistor disposed in electrical communication with the heater and a first pump electrode, wherein at least a portion of the resistor is disposed over at least two sides of the gas sensor.

33. A gas sensor comprising:
an electrochemical cell having a solid electrolyte layer disposed between an exhaust gas electrode and a reference electrode;
a protective layer disposed in contact with the exhaust gas electrode;
a via hold disposed through the protective layer;
a reference gas channel disposed in fluid communication with the reference electrode;

a heater disposed in thermal communication with the electrochemical cell; and a resistor disposed in electrical communication with the heater and the reference electrode, wherein at least a portion of the resistor is disposed over at toast two sides of the gas sensor.

34. A method of making a gas sensor comprising:

disposing an electrochemical cell having a solid electrolyte layer between an exhaust gas electrode and a reference electrode;

disposing at least one protective layer in contact with the exhaust gas electrode;

disposing a via hold through the protective layer;

disposing a reference gas channel in fluid communication with the reference electrode;

disposing a heater in thermal communication with the electrochemical cell;

disposing a resistor in electrical communication with the heater and a pump electrode, wherein at least a portion of the resistor is disposed over at least two sides of the gas sensor.

35. A method of making a gas sensor comprising:

disposing an electrochemical cell having a solid electrolyte layer between an exhaust gas electrode and a reference electrode;

disposing a protective layer in contact with the exhaust gas electrode;

disposing a via hole through the protective layer;

disposing a reference gas channel in fluid communication with the reference electrode;

disposing a heater in thermal communication with the electrochemical cell; and disposing a resistor in electrical communication with the heater and the reference electrode, wherein at least a portion of the resistor is disposed over at least two sides of the gas sensor.

* * * * *